United States Patent [19]

Eldridge, Jr.

[11] 4,447,238
[45] May 8, 1984

[54] MEDICAL TUBING HOLDER

[75] Inventor: John D. Eldridge, Jr., Balboa Island, Calif.

[73] Assignee: Instranetics, Inc., Tustin, Calif.

[21] Appl. No.: 226,493

[22] Filed: Jan. 19, 1981

Related U.S. Application Data

[63] Continuation-in-part of Ser. No. 147,632, May 7, 1980, Pat. No. 4,336,806.

[51] Int. Cl.³ ............................................. A61M 25/00
[52] U.S. Cl. ............................... 604/280; 604/174; 24/482; 24/303; 284/74.4; 335/303; 128/DIG. 26
[58] Field of Search ................ 128/348, DIG. 26, 214, 128/214.4, 221, DIG. 6; 24/201 B; 248/205 A, 75, 74 BB, 467; 269/8; 335/303, 285; 604/174, 179

[56] References Cited

U.S. PATENT DOCUMENTS

| 361,248 | 4/1887 | Winton | 335/285 |
|---|---|---|---|
| 2,597,601 | 5/1952 | Sherman | 335/303 X |
| 3,421,187 | 1/1969 | Ryder | 248/74 PB X |
| 3,430,300 | 3/1969 | Doan | 128/DIG. 26 X |
| 3,529,328 | 9/1970 | Davison | 24/137 R |
| 3,727,658 | 4/1973 | Eldridge, Jr. | 150/52 R |
| 3,826,254 | 7/1974 | Mellor | 128/DIG. 26 X |
| 3,878,849 | 4/1975 | Muller et al. | 128/349 R |
| 3,944,069 | 3/1976 | Eldridge, Jr. | 200/350 |
| 4,165,748 | 8/1979 | Johnson | 128/DIG. 26 X |
| 4,258,493 | 3/1981 | Kettlestrings et al. | 24/201 B |

FOREIGN PATENT DOCUMENTS 778279 2/1968 Canada ............................. 335/303

OTHER PUBLICATIONS

Pharmaseal K99, Tube and Cord Holder Device, Pharmaceal Lab., Glendale, Cal. 91201.

Primary Examiner—Stephen C. Pellegrino
Attorney, Agent, or Firm—Knobbe, Martens, Olson & Bear

[57] ABSTRACT

A medical tube holder and its method of use are disclosed. The holder has a backing element having front and back faces, a portion of the back face having means to adhere to a substrate. The element has an elongate elastic strip having a free end and an end attached to the element suitable for wrapping around tubing to form a loop within which the tubing is held. Members possessing a mutual magnetic attraction are mounted on the front surface of the element for mutual engagement when the element is folded. After the tube is positioned within the loop, the free end of the strip is pulled to tighten the loop and is then positioned between the magnetic members. When the element is folded, the strip is held between the magnetic members to lock the tube within the loop.

15 Claims, 6 Drawing Figures

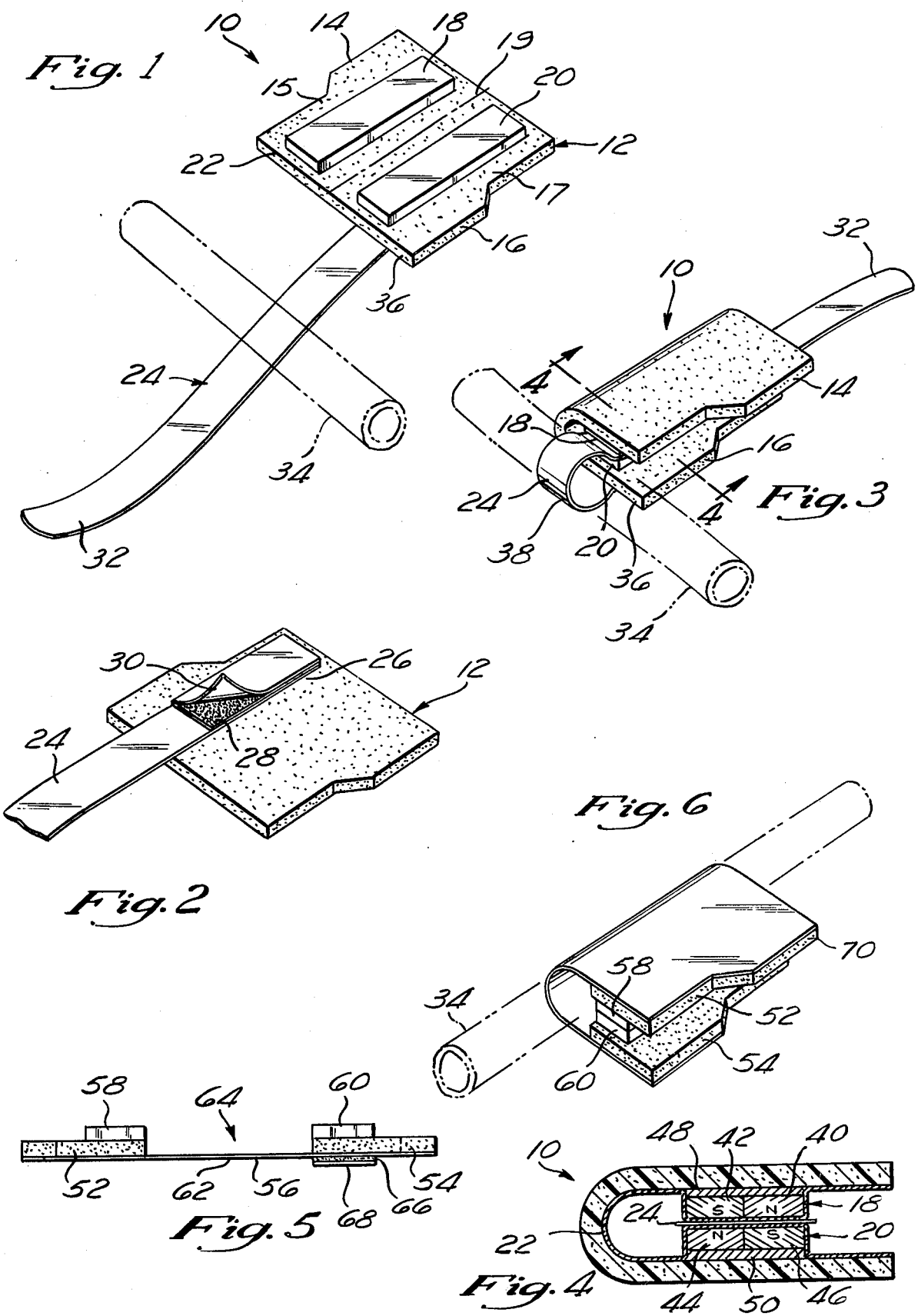

MEDICAL TUBING HOLDER

REFERENCE TO RELATED APPLICATIONS

This application is a continuation-in-part of copending application Ser. No. 147,632 entitled "Medical Tubing Holder" filed May 7, 1980 now U.S. Pat. No. 4,336,806.

BACKGROUND OF THE INVENTION

The invention generally relates to holders for medical tubing, such as vacuum tubes, electrical cords, and the like, which are often employed in surgical operations.

Throughout a hospital, tubing and cords of various types are used in health care operations and particularly during surgery. Often there is a need to be able to temporarily anchor such tubing. After being deposited, the tubing must be easily retrievable for further use during the particular operation and, in addition, there is a need to improve the ability of the physician or nurse involved in the operation to control and handle such tubing. Thus, it is often advantageous that the tubing be prevented from sliding while deposited. It is also advantageous to be able to control the amount of holding power of the anchoring device.

For example, vacuum tubes, which are used to remove accumulating blood or other fluids during surgery, must be readily accessible throughout the operation and yet not be an obstruction. Nasal gastric tubes are inserted into the patient's nostril and are used to siphon fluids from the patient's stomach. There is a need to be able to anchor and adequately control the nasal gastric tubing which extends from the patient's nostrils. If a cautery is employed during an operation, there is a need to be able to anchor and manipulate the cautery cord which extends from the instrument. A further example of tubes which require manipulation or anchoring are the tubes which extend from intravenous bottles that are used to provide nourishment to the patient.

One known prior device has a square support pad with front and back faces. An adhesive is applied to the back surface so that the pad can be affixed to a substrate, such as a surgical drape. The front or upper surface of the pad is made of felt. One portion of the support pad is a rectangular strip which can be wound around a tube. The end of the strip or pad has a Velcro ® pad which is attached to the felt surface, thereby holding the tube in place. The pad may be wound around the tube so as to contact the tube with a portion of the adhesive side or only the felt side of the strip, thereby determining whether the tube is permitted to slide within the strip while being held. Another device is composed of a strip of felt having a roughened Velcro ® flap attached at one end of the strip. Tubing is placed between the felt strip and flap and is secured by pushing the flap down into the felt to effect the Velcro ® lock.

Such devices have several problems since the Velcro ® has a tendency to snag the gloves used by the nurses and surgeons. In addition, the second device has no ability to anchor tubing without permitting it to slide. Moreover, with the first device, in order to affix a tube without permitting slide, the operator must work with a sticky adhesive that can snare the operator's gloves and the like. Finally, these devices do not allow the operator to control the amount of holding power applied to the tubing.

There is, therefore, a need for an effective device which will easily hold various sizes of medical tubing and yet prevent it from sliding while being held.

SUMMARY OF THE INVENTION

The disclosed invention obviates the difficulties involved in prior tubing holder devices. The device has a backing element with front and back faces, a portion of the back face including means for adhering to a substrate, such as a surgical drape. The element is flexible so as to be movable between folded and unfolded positions.

Members having a mutual magnetic attraction are mounted on the front surface of the element for mutual engagement when the element is folded. At least one member is a magnet with the other members being magnetizable materials.

An elastic strip is attached at one end to the element. The strip is of a sufficient length to permit it to be wrapped around a tube forming a loop within which the tube is held. The tube is positioned adjacent one side of the element and the free end of the strip is pulled until the loop tightens to hold the tube snugly against the element. The free end is placed over the upper surface of one of the magnetic members. The members are then closed together by folding the element to lock the strip between them and secure the tube within the tight loop.

The tubing is easily released from the holder by simply pulling up on finger tabs provided on the element, thereby disengaging the members from one another and unfolding the backing strip.

Due to the elasticity and length of the strip, it can accommodate the most common sizes of tubing used in a hospital. Moreover, if desired, multiple tubes of varying sizes may be held in the loop at one time. Advantageously, the elastic strip has a surface which will not permit the tubes to slide while being held. This is a significant improvement over Velcro ® lock devices which have a felt surface that permits the tube to slide. In addition, the effective holding power of the inventive device is accomplished without the use of sticky adhesives which can easily snag gloves, clothing and the like.

In another embodiment, employing multiple magnets, the magnets include a pair of contiguous magnetic portions of opposite polarity to produce maximum surface area contact of the magnets when the element is in its folded position. This insures that the elastic strip is held with maximum magnetic force by the magnets in the folded configuration, thereby providing for a secure lock on the tubing.

In a further embodiment, the strip is eliminated and the portion of the backing element between the magents formed of elastic. This elastic portion forms a tube receiving location. When a tube is placed within the location, the element is folded to permit the magnets to mutually engage. This secures the tubing between the folded sections of the element. Since the tube receiving location is elastic, large sizes of tubes can easily be held. Moreover, multiple tubes can be held at one time if desired.

The inventive holder is useful in anchoring the various tubes and cords employed in a hospital. Moreover, a plurality of backing elements may be mounted within an instrument sterilization case to hold various types of medical instruments.

DESCRIPTION OF THE DRAWINGS

These and other advantages will be clarified by the discussion below and reference to the drawings in which:

FIG. 1 is a perspective view of a preferred embodiment of the inventive device, showing the backing element and magnets mounted thereon with the elastic strip depending from the element and a piece of tubing in position to be enveloped and held;

FIG. 2 is a perspective view of the back side of the device of FIG. 1 showing a peel-away adhesive portion;

FIG. 3 is a perspective view of the backing element of FIG. 1 in its folded position with a tube anchored within the loop formed by the elastic strip;

FIG. 4 is a cross-sectional view taken along line 4—4 of FIG. 3 showing the magnets with their respective polarities in mutual engagement;

FIG. 5 is a side view of an alternate embodiment of the device having an elastic portion located between the magnets; and FIG. 6 is a perspective view of the device of FIG. 5 in its folded position holding a tube.

DETAILED DESCRIPTION OF THE PREFERRED EMBODIMENTS

Referring to FIG. 1, a tubing holder device 10 is shown. The holder 10 has a backing element 12 which is generally rectangular in shape except for finger tabs 14 and 16 which protrude outward at diagonally opposed corners of the backing element 12. The purpose of the finger tabs 14, 16 will hereinafter be described.

The backing element 12 is a sheet of porous foam plastic material, such as foamed polyurethane. Such material is flexible and light in weight. It should be understood that although the backing element 12 is an integral piece of foam, it may be conceptualized for the purpose of description as having two sections 15, 17 which are mutually folded along a junction 19 located about midway between them. As shown in the preferred embodiment a first magnet 18 is mounted on the first section 15 of the backing element 12 and a second magnet 20 is mounted on the second section 17. The magnets 18, 20 are mounted on the backing element 12 so as to be in mutual engagement when the element 12 is folded along the junction 19.

The magnets 18, 20 are held in place on the backing element 12 by an impervious thin plastic laminate 22 which is vacuum-formed around each magnet. The laminate 22 is drawn into intimate contact with the backing element 12 between the magnets by application of suction pressure under the backing element 12.

An elongate elastic strip 24 depends from the undersurface of the backing element 12. As shown in FIG. 2, the strip 24 has an end portion 26 which is attached to the underside of the backing element 12. The attached end 26 may be joined to the backing element 12 in any suitable manner, such as, by applying adhesive. This strip 24 is made of a flexible, stretchable, resilient material. Thus, the strip 24 will conform to the size and shape of the tubing to be held.

As shown in FIG. 1, the elastic strip 24 also has a free end 32 which is suspended from the backing element 12. The strip 24, in the preferred embodiment, is approximately 5 inches in length, and is more than about twice the length or width of the backing element 12. The strip 24 has a slightly greater width than the width of the magnets 18, 20. The end portion 26 is located and attached below the second magnet 20; that is, its longitudinal axis is parallel to and offset vertically below the longitudinal axis of the second magnet 20.

As shown in FIG. 2, an adhesive coating 28 is applied to the upper surface of the attached end 26 of the strip 24. A peel-away silicone treated paper 30 is then applied over the adhesive 28. In use, the paper 30 is removed to expose the adhesive 28. The adhesive 28 is then pressed against a substrate, such as a surgical drape, to affix the second section 17 of the backing element 12 to the substrate. The first section 15 remains movable to allow the element to be folded as will hereinafter be described. It should be understood that the holder may be held to a substrate by other suitable means, both magnetic and mechanical, e.g. clips, snaps, etc.

To use the device, hospital personnel would typically affix the element 12 to a substrate, such as a surgical drape, using the adhesive 28. The user then positions a tube 34 on the strip 24 so that its axis is essentially perpendicular to the axis of the strip 24 as shown in FIG. 1. The strip 24 is then wrapped around the outside of the tube 34, forming a loop within which the tube 34 is held. The free end 32 is pulled across the length of the magnet 20 tightening the loop until the tube 34 is held snugly. Typically, the tube 34 should be manually held during this operation against a side 36 of the element 12 located between the tube 34 and the magnet 20. This prevents the tube 34 from rolling over the side 36 and onto the magnets 18, 20. Next, the free end 32 is laid against the upper surface of the second magnet 20. The element 12 is then folded along the junction 19 so that the first section 15 is above the second section 17. This brings the first and second magnets 18, 20 into mutual engagement anchoring the strip 24 between the magnets 18, 20. If desired, the device may be used without affixing it to a substrate. Thus, the element 12 may be grasped between the thumb and index finger of the operator and the tube held adjacent the side 36. The free end 32 is then wrapped around the tube 34 and placed over the magnet 20 as described above. The tube 34 is then held securely by folding the magnets 18, 20 together to clamp the free end 32.

As shown in FIG. 3, the holder 10 is in its folded configuration. The tube 34 is held tightly against the element side 36 within a loop 38 formed by the elastic strip 24. The strip 24 is held tightly between the magnetic members 18, 20, which are in mutual confrontation separated only by the strip 24. The excess of the free end 32 extends outward a distance beyond the element 12.

The elastic strip 24 advantageously has a surface which prevents the tube 34 from sliding within the loop 38. This is an important feature since it increases the control the user has over the tubing. The surface of the strip 24 is also important in that it does not easily slide over the laminate surface 22. The laminate 22 and the surface of the strip cooperate to keep the strip 24 locked between the members. Thus, with the element 12 folded, as shown in FIG. 3, it is extremely difficult to pull the strip 24 out from between the magnets 18, 20. This in turn ensures that the loop 38 remains tightly wrapped around the tube 34.

Since the elastic strip is formed of a stretchable resilient material, the device can accommodate larger sizes of tubing. Moreover, multiple tubes may be held at one time. Thus, the strip stretches to accommodate several tubes, if necessary, and will return to its normal length following use due to the memory of the material.

As described, the elastic strip 24 is parallel to and directly below the second magnet 20. This alignment allows the strip 24 to be easily wrapped around a tube and placed over the surface of the magnet 20 and prevents the strip 24 from tending to kink or bind in the holding process.

Referring again to FIG. 3, the tube 34 is released by simply pulling up on the finger tab 14, and unfolding the element 12. This releases the elastic strip 24 and frees the tube 34. The holding power of the device can be altered by increasing or decreasing the mutual attraction between the magnets 18 and 20.

FIG. 4 depicts a cross-sectional view of the holder 10 in its folded configuration with the first magnet 18 in mutual engagement with the second magnet 20. It has been found convenient to use magnets formed of magnetic particles bonded together by elastomeric material. For example, magnets formed of nitrile rubber embedded with particles of ferromagnetic material such as, barium ferrite, have been found to be highly satisfactory. Magnets of this type may be polarized so that the lower surface which rests on the backing element 12, constitutes one pole, and the upper surface constitutes the other pole. The magnets are cut to form elongated bars or strips.

Advantageously, each magnet includes a pair of magnet portions in which upper and lower surfaces have been aligned for opposite polarity. These portions may be separate members or joined integrally. Thus, the first magnet 18 is composed of a magnet portion 40 having a north polarity on its upper surface and a south polarity on its lower surface which is contiguous with a magnet portion 42 having a south polarity on its upper surface and a north polarity on its lower surface. For simplification, only the upper surface polarities are identified. The second magnet 20 has a magnet portion 44 of upper surface north polarity and lower surface south polarity and a magnet portion 46 of upper surface south polarity and lower surface north polarity.

As the holder is folded, the portion 44 of the second magnet 20 is attracted to the portion 42 of the first magnet 18. Similarly, the portion 46 of the second magnet 20 is attracted to the portion 40 of the first magnet 18. The upper surface north/south polarities of the portions 40, 42 of the first magnet 18 are oppositely positioned to the upper surface north/south polarities of the portions 44, 46 of the second magnet 20 when the holder 10 is in its folded configuration. Thus, when the backing element 12 is folded, the positioning of the magnets portions ensures that the first and second magnets 18, 20 will have maximum surface area contact. This maximum contact increases the power with which the strip 24 is held between the magnets 18, 20. Moreover, it also ensures that the backing element 12, when folded, is properly aligned as shown in FIG. 3. Thus, if the upper surface of the first magnet 18 were of a single polarity, and the upper surface of the second magnet 20 were of a single but opposite polarity, when the backing element 12 would be folded, the magnets would hold each other irrespective of their relative positions. Thus, folded sections could be misaligned, i.e., not directly on top of one another.

Underlying each magnet is a magnetizalbe backing member. As shown in FIG. 4, the magnetizable backing member 48 underlies the first magnet 18, and the magnetizable backing member 50 underlies the second magnet 20. The magnetizable backing members block the magnetic field from extending through the back surface of the backing element 12. This increases the magnetic field of the overlying magnet three to four times.

Referring to FIG. 5, an alternate embodiment of the holder is shown. The device has a first section of foam 52 and a second section of foam 54 spaceably mounted on an elastic backing member 56. A first magnet 58 is mounted on the first section of foam 52 and a second magnet 60 is mounted on the second section of foam 54.

The foam sections 52, 54 are of the same materials as the element 12 shown in FIG. 1. The elastic backing member 56 can be folded at a junction 62 which is approximately mid-way between the first and second sections 52, 54. The elastic backing member 56, like the strip 24, is flexible, rubbery, resilient and advantageously has a surface which does not permit tubing to slide.

The elastic backing member 56 has an area 64 located between the first and second sections 52, 54 which is a receiving location for tubing. Tubing positioned on this location will lie between the first and second magnets 58, 60 when the backing element is in its folded configuration as will hereinafter be described.

The magnets 58, 60 may advantageously have magnet portions of opposite surface polarity and magnetizable members as discussed above with reference to FIG. 4.

Attached beneath the second section 54 is an adhesive 66 which is covered with a peel-away silicone treated paper 68. The paper 68 and adhesive material 66 are used to affix the backing element to a substrate in the same manner as discussed above with reference to FIG. 2.

To use the device, the section of tubing 34 is positioned within the receiving location 64 between the first magnet 58 and the second magnet 60. Referring to FIG. 6, the first section 52 supporting the first magnet 58 is folded over the second section 54 supporting the second magnet 60. In this position, the first and second magnets 58, 60 are mutually engaged. The attraction of the first magnet 58 for the second magnet 60 maintains the holder in its folded position and thereby secures the tubing 34 between the folded portions within the receiving location 64. Since the receiving location 64 is formed of an elastic material, the location can stretch to accommodate various sizes of tubing. Moreover, the embodiment is able to handle multiple tubes at one time. This is an important advantage of this embodiment over the device described in applicant's co-pending application Ser. No. 147,632, the disclosure of which is herewith incorporated by reference. Finally, the surface of the elastic backing 56 prevents the tube 34 from sliding while being held.

When one desires to remove the tubing, one may simply pull upward on a finger tab 70, thereby unfolding the holder into its co-planar position, as shown in FIG. 5.

What is claimed is:

1. A medical tube holder comprising:
    (a) a backing element movable between folded and unfolded positions having first and second members with a mutual magnetic attraction spaced for mutual engagement when the element is folded; and
    (b) an elongate strip having a free end and an end attached to said element, said strip being long enough to wrap around a tube to form a loop within which said tube is held and to permit said free end to be held between said engaged members locking said tube within said loop, said strip being parallel to and offset from the longitudinal axis of one of said members.

2. A medical tube holder comprising:
(a) a backing element movable between folded and unfolded positions having first and second members with a mutual magnetic attraction spaced for mutual engagement when the element is folded along a fold line; and
(b) an elongate strip having a free end and an end attached to said element, said strip being long enough to wrap around a tube to form a loop within which said tube is held and to permit said free end to be held between said engaged members locking said tube within said loop, said fold line being parallel to and offset from the longitudinal axis of said strip.

3. A holder for medical tubing comprising:
(a) a foldable backing element having a single fold line;
(b) members with mutual magnetic attraction, first and second of such members being attached to said backing element and spaced apart thereon so as to be superimposed, one above the other, when the element is folded along said line; and
(c) an elongate strip having a free end and an end attached to said element;
wherein when said tubing is placed across said extended strip between said free and attached ends all said members are on one side of the tubing remote from said free end and said strip is long enough to wrap, and form a loop, around said tubing and to permit said free end to be held between said superimposed members to hold said tubing in said loop.

4. The holder of claim 1, 2 or 3 wherein said strip is elastic to permit it to stretch.

5. The holder of claim 1, 2 or 3 wherein said strip and said magnetic members have surfaces which cooperate to prevent said strip from slipping out from between said members.

6. The holder of claim 1, 2 or 3 wherein said strip has a surface which prevents said tube from easily sliding within said loop.

7. A holder for medical tubing comprising:
(a) a foldable, plastic foam backing element bearing first and second members with mutual magnetic attraction and spaced apart so as to be superimposed, one above the other, when said element is folded along a fold line, said members being covered with a thin, impervious layer of plastic material;
(b) an elastic elongate strip having a free end and an end attached to said element in a manner such that the longitudinal axis of said strip is in alignment with said first member and offset from said second member, said strip being long enough to be looped around said tubing to retain said tubing therein and to be held between said members when they are superimposed by folding said element, the material of said strip and said thin plastic material assisting the attraction between said members to prevent slipage of said strip between said members.

8. The holder of claim 1, 2, 3 or 7 further comprising means for holding said element to a substrate, said holding means being attached to the back surface of said element.

9. The holder of claim 8 wherein said holding means is an adhesive.

10. The holder of claim 1, 2, 3 or 7 wherein said first member is a magnet.

11. The holder of claim 10 wherein said second member is a magnet.

12. The holder of claim 10 wherein said first member has an underlying magnetizable strip to increase the magnetic character of said member.

13. The holder of claim 11 wherein said first member includes a pair of magnet portions of opposite surface polarity, and wherein said second member includes a pair of magnet portions of opposite surface polarity, said members being mutually oriented so that when a tube is in place in the folded holder, the mutually attracting magnet portions of each member are in alignment to maximize surface area contact between the members and position said portions one on top of another.

14. The holder of claim 13 wherein said magnet portions of each pair are contiguous.

15. The holder of claim 1, 2, 3 or 7 wherein said backing element or elements has tab portions to be grasped for opening said holder to release said tube.

* * * * *